United States Patent [19]

Nemec et al.

[11] 4,010,082
[45] Mar. 1, 1977

[54] DIVINYLACETYLENES AS POLYMERIZATION INHIBITORS FOR ACRYLIC AND METHACRYLIC ACID

[75] Inventors: Joseph W. Nemec, Rydal; Thomas Stewart, Andalusia, both of Pa.

[73] Assignee: Rohm and Haas Company, Philadelphia, Pa.

[22] Filed: Aug. 21, 1975

[21] Appl. No.: 606,627

[52] U.S. Cl. .............................. 203/8; 203/DIG. 21; 260/526 N
[51] Int. Cl.² ...................... C07C 57/04; B01D 3/34
[58] Field of Search ......... 203/8, 9, 70, 6, DIG. 21; 260/526 N, 679 R, 679 A; 252/399

[56] References Cited

UNITED STATES PATENTS

| | | | |
|---|---|---|---|
| 2,805,190 | 9/1957 | Monroe | 203/9 |
| 3,117,167 | 1/1964 | Burch | 260/679 |
| 3,150,166 | 9/1964 | Pohlemann | 260/526 N |
| 3,227,628 | 1/1966 | Hess | 260/526 N |

*Primary Examiner*—Wilbur L. Bascomb, Jr.

[57] ABSTRACT

A method is disclosed for inhibiting the polymerization of acrylic and methacrylic acids at ambient or above ambient temperature, such as during preparation, purification or storage of the acids under substantially anaerobic conditions, by adding thereto a polymerization inhibiting amount of a compound having the formula:

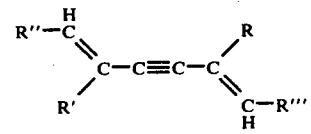

where R, R′, R″, R′″ are hydrogen, alkyl or aryl.

6 Claims, No Drawings

DIVINYLACETYLENES AS POLYMERIZATION INHIBITORS FOR ACRYLIC AND METHACRYLIC ACID

This invention relates to the use of divinylacetylenes for preventing the polymerization of acrylic and methacrylic acid at ambient and above ambient temperatures, such as may occur in preparation, purification or storage of the acids under substantially anaerobic conditions.

Acrylic and methacrylic acid are well-known and their preparation has been amply disclosed in the literature and art. As all these processes require elevated temperatures to produce the desired product, polymerization of reaction product in the reaction zone due to heating above ambient temperatures is a persistent problem in monomer manufacture. Further, the almost universal method for purification of the crude and impure acids obtained by various processes involves the step of distillation. The problem encountered during this step, which generally entails refluxing at elevated temperatures, is again the marked tendency for these monomers to polymerize. The polymerization occurs in the still pots and in the distillation columns. This polymer induces a high strain on processing equipment, such as pumps, necessitating frequent shutdowns. Polymer formation on the distillation column plates likewise entails costly shutdowns and cleanings. These monomers also tend to polymerize at ambient temperatures during even short periods of storage in the absence of inhibitors.

A variety of polymerization inhibitors have been developed and are known in the art. Very useful inhibitors include aromatic phenols, aromatic amines and various quinones. However, these compounds are relatively ineffective in preventing polymerization of acrylic and methacrylic acid when anaerobic conditions are encountered. In many processes, both for preparation and purification, as well as in storage, an adequate supply of air cannot be ensured. As most of the known inhibitors depend on oxygen to carry out their inhibiting effect, a lack of oxygen, such as under anaerobic conditions, leads to almost total loss of their inhibitory properties. Such anaerobic conditions are common in processing equipment, such as in vapor spaces, overheads, unvented reflux columns and especially when vacuum distillations are involved. It is in these areas that polymers tend to form when oxygen-requiring inhibitors are used without an adequate supply of oxygen.

According to the present invention, a method of inhibition is provided which is useful in preventing polymerization of acrylic and methacrylic acid during their preparation, purification and storage under substantially anaerobic conditions at ambient or above ambient temperatures. The method involves contacting the acids as an impure mixture or in pure form, with an amount of a known divinylacetylene effective to inhibit polymerization.

The useful inhibitors are compounds having the formula:

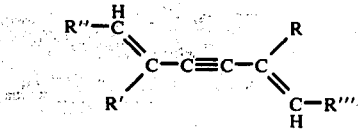

where R, R', R'', R''' are hydrogen, alkyl or aryl. The alkyls are preferably lower aliphatic groups having one to five carbon atoms, the aryls are preferably groups having six to 10 carbon atoms, and the phenyl group is most preferred. Examples include 1,5-hexadien-3-yne, 2,6-octadien-4-yne, 2,5-dimethylhexa-1,5-dien-3-yne, 3,6-dimethylocta-2,6-dien-4-yne, 1,2-diphenylhexa-1,5-dien-3-yne, 2,5-diphenylhexa-1,5-dien-3-yne, 2-phenylhexa-1,5-dien-3-yne, 2-methylhexa-1,5-dien-3-yne, 2-t-butylhexa-1,5-dien-3-yne and so forth.

The lower alkyl members are especially preferred as they are volatile and will readily reach into anaerobic equipment areas such as vapor spaces and overheads. The useful inhibitors can be used in a range of about 0.01 to about 0.5% by weight based upon the weight of the acid. A preferred concentration is about 0.1%, as this concentration is entirely sufficient to inhibit polymerization.

As previously discussed, the inhibitors of this invention may be employed to inhibit polymerization during the preparation of acrylic or methacrylic acid, as well as during the purification of these monomers by distillation. The inhibitors can be contacted with crude impure monomer in the still kettle of the distillation system prior to distillation. The inhibitors may also be added to the plates of the distillation column during distillation to prevent polymer formation therein. While the inhibitors of the invention do not always completely suppress the formation of the acrylic or methacrylic polymers, even if polymers do form it is only after a considerably longer period of time than can be obtained by other known inhibitors or in the absence of any inhibitor. Additionally, purified monomers are effectively stabilized against polymerization during storage under anaerobic conditions at ambient temperature by the addition of the inhibitors of this invention.

In the following example comparative tests are run to show the effect of these inhibitors upon acrylic acid under anaerobic conditions such as might be encountered during distillation or under storage.

EXAMPLE I

An aliquot (2 mls) of acrylic acid containing inhibitor and initiator (0.1% azobisisobutyronitrile) is placed in a reaction vessel and sparged with nitrogen to remove dissolved oxygen. After sparging, the solution is contained under a nitrogen blanket. The vessel is heated at 75° C. with a thermocouple device for measuring the solution temperature. When the monomer polymerizes, it releases heat and the increase in solution temperature relative to a blank is recorded. The beginning of this exotherm is considered the Onset Time noted in Table I below. The Inhibition Time is the difference between the Onset Time from the monomer containing inhibitor and that of uninhibited monomer.

TABLE I

| | Acrylic Acid Containing 0.1% Azobisisobutyronitrile and Inhibitor | | |
|---|---|---|---|
| INHIBITOR | % CONCENTRATION | ONSET TIME (mins) | INHIBITION TIME |
| Uninhibited | 0 | 5 | 0 |
| 2,5-dimethylhexa-1,5-dien-3-yne | 0.1 | 26 | 21 |
| 3,6-dimethylocta-2,6-dien-4-yne | 0.1 | 19 | 14 |
| Hydroquinone monomethyl ether | 0.1 | 5 | 0 |
| Hydroquinone | 0.1 | 5 | 0 |
| Quinone | 0.1 | 15 | 10 |

From the inhibition times it is apparent that the divinylacetylenes are improvements over the prior art inhibitors under anaerobic conditions. It is recognized that quinone is a useful anaerobic inhibitor and it can be seen that these compounds are also more effective than quinone.

We claim:

1. A method for inhibiting the polymerization of acrylic and methacrylic acid at ambient or above ambient temperatures, said method comprising contacting said acid with a polymerization inhibiting compound having the formula:

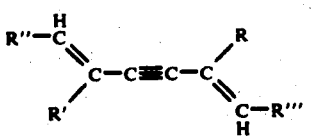

where
R, R', R", R''' is hydrogen, alkyl or aryl, in an amount effective to inhibit polymerization of the acid during the preparation, purification or storage of said acid under substantially anaerobic conditions.

2. The method of claim 1, wherein the purification of the acids is by distillation employing reflux.

3. The method of claim 1 wherein the polymerization inhibiting compound is 2,5-dimethylhexa-1,5-dien-3-yne.

4. The method of claim 1, wherein the polymerization inhibiting compound is 3,6-dimethylocta-2,6-dien-4-yne.

5. The method of claim 1, wherein the polymerization inhibiting compound is used in an amount of from 0.01 to 0.5% by weight based upon the weight of the acid.

6. The method of claim 1, where said polymerization inhibiting compound is added to an impure mixture of said acid and said acid is distilled under substantially anaerobic conditions and condensed outside of the distillation zone.

* * * * *